United States Patent
Johnston et al.

[11] Patent Number: 5,941,904
[45] Date of Patent: Aug. 24, 1999

[54] ELECTROMAGNETIC ACCELERATION TRANSDUCER FOR IMPLANTABLE MEDICAL DEVICE

[75] Inventors: Matthew M. Johnston, Angleton; Don C. Deno, Missouri City; Alex Zinner, Deer Park, all of Tex.

[73] Assignee: Sulzer Intermedics Inc., Angleton, Tex.

[21] Appl. No.: 08/928,880

[22] Filed: Sep. 12, 1997

[51] Int. Cl.[6] .............................. A61B 5/05; A61B 5/02; A61N 1/05
[52] U.S. Cl. .......................... 607/19; 607/119; 607/122; 324/207.11; 324/207.15
[58] Field of Search ............................ 607/19, 35, 119, 607/122; 324/707.11, 207.15; 73/514.17

[56] References Cited

U.S. PATENT DOCUMENTS

| | | |
|---|---|---|
| 3,673,873 | 7/1972 | Estes et al. . |
| 3,835,864 | 9/1974 | Rasor et al. . |
| 4,397,185 | 8/1983 | Craig et al. ............................ 73/504 |
| 4,600,017 | 7/1986 | Schroeppel . |
| 4,936,304 | 6/1990 | Kresh et al. . |
| 5,014,700 | 5/1991 | Alt . |
| 5,031,615 | 7/1991 | Alt . |
| 5,044,366 | 9/1991 | Alt . |
| 5,304,208 | 4/1994 | Inguaggiato et al. ...................... 607/17 |
| 5,496,351 | 3/1996 | Plicchi et al. . |
| 5,496,361 | 3/1996 | Moberg et al. . |
| 5,549,652 | 8/1996 | McClure et al. . |
| 5,628,777 | 5/1997 | Moberg et al. . |
| 5,792,199 | 8/1998 | Fayram et al. . |

FOREIGN PATENT DOCUMENTS 2478996  10/1981  France .

OTHER PUBLICATIONS

David M. Salerno, M.D. Ph.D. and John Zanetti, M.S.; Seismocardiography for Monitoring Changes in Lef Ventricular Function during Ischemia; Oct., 1991; pp. 991–993.

*Primary Examiner*—William E. Kamm
*Assistant Examiner*—Carl H. Layno
*Attorney, Agent, or Firm*—Schwegman, Lundberg, Woessner & Kluth, P.A.

[57] ABSTRACT

An electromagnetic accelerometer includes a rigid shell with a cavity in which two magnets are fixed at either and of the rigid shell and one magnet is allowed to move between the fixed magnets. The three magnets are arranged so that the movable magnet is suspended between the fixed magnets by magnetic forces from the fixed magnets. A coil of wire surrounds the shell and magnets. An acceleration of the accelerometer causes a displacement of the movable magnet with the cavity. As a result, an electrical current is induced in the coil of wire. The voltage in the coil of wire is proportional to the acceleration experienced by the accelerometer. The electromagnetic accelerometer is particular useful in an implantable pacemaker or defibrillator and can be included in either or both a lead or the housing of the pacemaker. Further, the accelerometer generates its own voltage in response to acceleration and the resulting electrical energy can be used as a power source.

17 Claims, 5 Drawing Sheets

FIG. 6

ELECTROMAGNETIC ACCELERATION TRANSDUCER FOR IMPLANTABLE MEDICAL DEVICE

BACKGROUND OF THE INVENTION

1. Field of the Invention

The present invention relates generally to an acceleration transducer. More particularly, the present invention relates to an electromagnetic accelerometer. Still more particularly, the present invention relates to an electromagnetic accelerometer for use in implantable medical devices.

2. Description of the Related Art

Acceleration transducers, commonly refer to as accelerometers, generate an electrical output signal corresponding to an acceleration experienced by the transducer caused by an externally applied force. Typically, the magnitude of the voltage of the electrical output signal is portional to the acceleration. Thus, by monitoring the magnitude of the voltage of the transducer's output signal, a measure of the acceleration experienced by the transducer can be determined.

Accelerometers are used in a variety of applications such as in some implantable medical devices including pacemakers and defibrillators (collectivity referred hereafter simply as pacemakers). Pacemakers use accelerometers for several reasons. First, an accelerometer may be included as a body activity sensor within the pacemaker's housing or "can" which encloses and seals the electronic circuitry of the pacemaker. An accelerometer-based body activity sensor provides an output signal that is proportional to the overall motion of the patient's body. The output signal from such a body activity sensor can be processed to distinguish a sleeping patient, for example, from a patient engaging in strenuous exercise with a high level of body motion. Rate-responsive pacemakers increase or decrease the rate of pacing (i.e., the rate at which the pacemaker emits electrical pulses to force a chamber of the heart to beat) in response to the measured index. A body activity accelerometer can be used to provide a control signal for a rate-responsive pacemaker keyed to body motion. Using a body activity accelerometer, a rate-responsive pacemaker can determine when the patient is engaging in strenuous exercise, and accordingly, increase the rate of pacing to meet the increased metabolic load of the patient during exercise. By contrast, the same rate-responsive pacemaker reduces the rate of pacing when the patient exhibits little motion such as during sleep when the patient's heart preferably beats less often. Examples of accelerometers used as body activity sensors are disclosed in U.S. Pat. Nos. 5,014,700, 5,031,615, and 5,044,366.

Accelerometers also are used for other purposes in pacemaker systems. Several attempts have been made at incorporating an accelerometer in a pacemaker lead which couples the pacemaker to the heart. A pacemaker lead typically is a thin flexible cable including one or more electrical conductors. One end of the lead couples to a header plug on the pacemaker can and the other end of the lead includes one or more conductive electrodes. A lead-based accelerometer can be used to measure the acceleration of the wall of the heart to which the lead is coupled. It is also known that lead accelerometers can be used to determine various physiological parameters such as contractility and ejection fraction. Further, an accelerometer incorporated into a lead can also be used to determine if the chamber of the heart in which an electrode is implanted has contracted in response to a pacing pulse generated by pacemaker. This determination is referred to as "capture verification."

U.S. Pat. No. 5,304,208 discloses a lead-based accelerometer coupled to an electronic pre-amplification network. This accelerometer, however, requires an extra pair of conductors to be included within the pacemaker lead to couple the accelerometer and associated electronics to the pacemaker can. It is generally recognized that there is a risk that once implanted a conductor within a lead may break disrupting the operation of the pacemaker and requiring surgical repair. Such surgery obviously increases risk and discomfort of the patient. Further, the risk of conductor breakage increases as the number of conductors in a lead increases. Reducing the number of conductors in a cardiac lead thus is highly desirable to improve the reliability of a pacemaker system. Moreover, the risk of conductor breakage in a lead is reduced if fewer conductors are included in a lead.

Many accelerometers, such as the accelerometer of U.S. Pat. No. 5,304,208, require electrical power for their operation. Implantable pacemakers and defibrillators typically operate from batteries housed within the can of the pacemaker. Because batteries store only a finite amount of electrical energy, it is highly desirable for pacemakers to use as little power as possible. Thus, pacemakers are designed for minimum power consumption. Accelerometers, such as that used in U.S. Pat. No. 5,304,208, that require electrical power for their operation are not desirable for this reason.

The output signal from an accelerometer typically requires amplification and filtering to condition the accelerometer's output signal for use by the pacemaker. Amplification and filtering circuitry requires electrical power to operate, thereby imposing an additional power drain on the pacemaker's batteries. Thus, it is desirable for transducers associated with a pacemaker, such as an accelerometer, to produce an electrical output signal that requires as little amplification and/or filtering as possible.

Accordingly, an accelerometer is needed, especially for use in implantable medical devices, that solves the shortcomings discussed above. Such an accelerometer should be small enough to be included in a typical cardiac lead coupling a pacemaker to the heart for capture verification or for determining various hemodynamic parameters. If incorporated into a lead, such an accelerometer preferably should require a minimal number of conductors in the lead. Further, such an accelerometer should require little, if any, operational power, thereby causing little or no drain on the pacemaker's battery. Battery drain could be further minimized if the accelerometer generates an output signal requiring little amplification and filtering.

SUMMARY OF THE INVENTION

Accordingly, there is herein provided an electromagnetic accelerometer that includes a rigid shell with a cavity in which two magnets are fixed at either end of the rigid shell and a third magnet is allowed to oscillate (reciprocate) between the fixed magnets. The three magnets are arranged so that, when the accelerometer is not being accelerated, the movable magnet is held suspended between the fixed magnets by magnetic forces from the fixed magnets. A coil of wire surrounds the shell and magnets. A change in velocity of the accelerometer causes a displacement of the movable magnet within the cavity. As a result, an electrical current is induced in the coil of wire. The voltage in the coil of wire is proportional to the acceleration experienced by the accelerometer. The electromagnetic accelerometer is particular useful in implantable pacemaker or defibrillator and can be included in either a lead or the housing of the pacemaker.

Further, the accelerator generates its own voltage in response to acceleration and the voltage can be used as a power source.

BRIEF DESCRIPTION OF THE DRAWINGS

Other objects and advantages of the invention will become apparent upon reading the following detailed description and upon reference to the accompany drawings, wherein.

DETAILED DESCRIPTION OF THE PREFERRED EMBODIMENT

Figure 1:
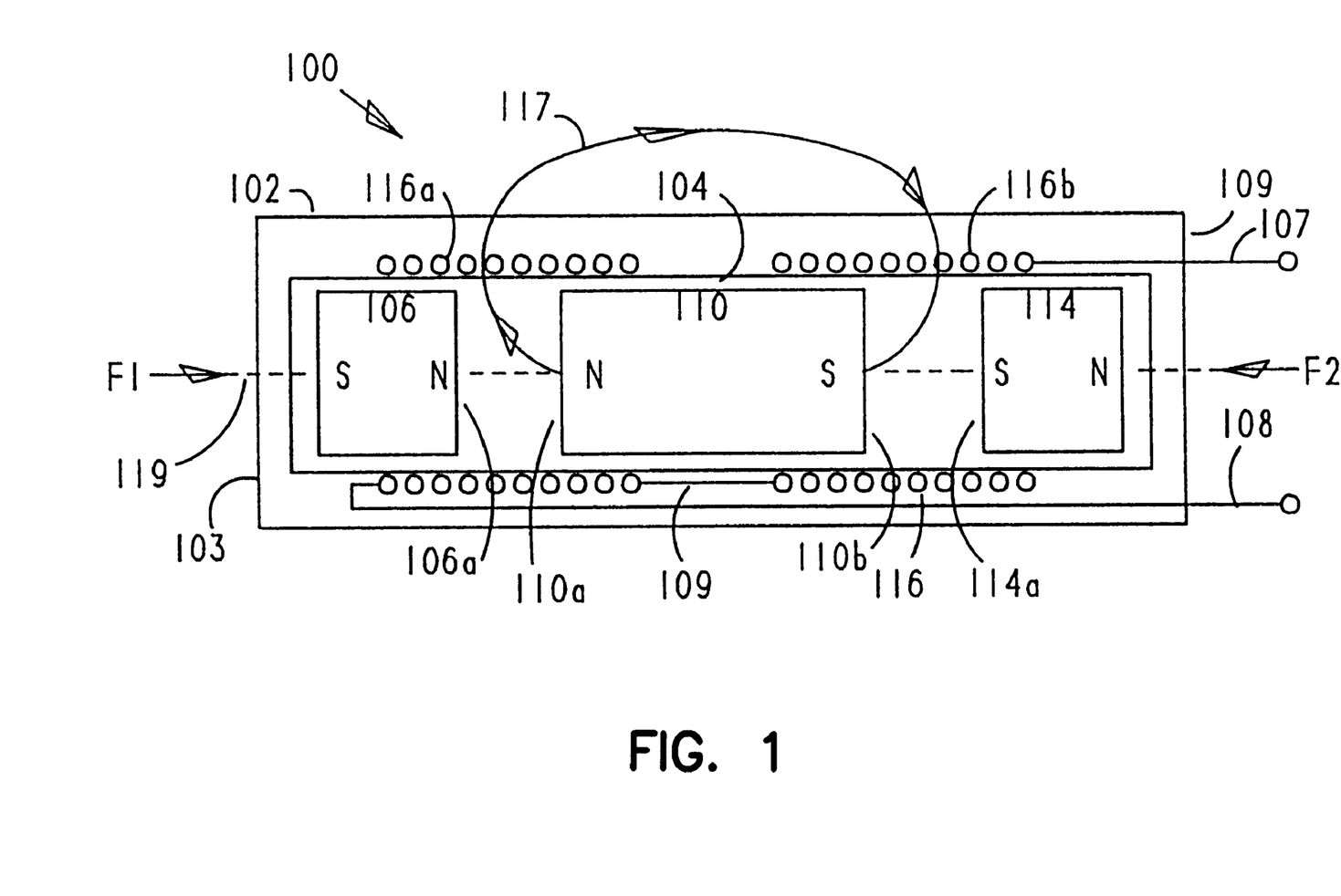
FIG. 1 is a cross-sectional view of the accelerometer in accordance with a preferred embodiment.

Referring now to FIG. 1, an electromagnetic accelerometer 100 constructed in accordance with a preferred embodiment generally includes a shell or housing 102 and a cavity 104 in which three magnets 106, 110, and 114 are housed. Magnets 106, 110, and 114 are arranged colinearly as shown. A coil of conductive wire is disposed about cavity 104. The shell 102 preferably is constructed of a rigid, hermetically-sealed material, such as ceramic, and is appropriately sized to fit either within an implantable lead or a pacemaker can. Coil 116 may impregnate shell 102. Alternatively, shell 102 may include a space between the shell and the cavity through which the coil is wound.

The coil of wire 116 preferably is constructed of fine insulation-coated conductive wire axially wound about cavity 104 in the matter shown in FIG. 1. Conductors 107 and 108 provide the output signal from accelerometer 100 and couple directly to opposite ends of the coil of wire 116. Coil 116 preferably includes two, spaced-apart coil sections 116a and 116b connected by conductor 109. Coil section 116a is wrapped about cavity 104 generally near the adjacent ends 106a and 110a of magnets 106 and 110, respectively. Coil section 116b is wrapped about cavity 104 generally near adjacent ends 110b and 114a of magnets 110 and 114, respectively. The placement of the coil sections 116a and 116b and conductor 109, the size of the wire comprising the coil, the material from which the coil is made, and the number of winds of the coil is determined to maximize the output voltage signal of the accelerometer 100 as will be discussed below in more detail. Instead of a coil of wire, coil 116 may be constructed from electrodeposition of conductive traces on an insulating substrate in a coil-like arrangement.

Referring still to FIG. 1, magnets 106 and 114 are fixed within cavity 104 at opposite ends of the cavity. Fixed magnets 106, 114 are bonded to opposite ends of cavity 104 using epoxy or suitable other adhesive. Magnet 110, however, is not fixed to cavity 104 and thus is movable and allowed to reciprocate or oscillate within the cavity 104 in response to externally applied forces on the accelerometer 100. Cavity 104 is lined with friction-reducing material, such as Teflon or other fluoropolymer. Fixed magnets 106, 114 and movable magnet 110 preferably are manufactured from sintered rare earth ceramic, or similar materials.

As is commonly known, a magnet has a south pole and a north pole. The south and north poles of magnets 106, 110, 114 are shown in FIG. 1 with S denoting the south pole and N denoting the north pole of each magnet. The magnets 106, 110, 114 are arranged within cavity 104 so that like poles coincide between adjacent magnets. Thus, the north pole of fixed magnet 106 is adjacent the north pole of movable magnet 110 and the south pole of fixed magnet 114 is adjacent the south pole of movable magnet 110. Alternatively, the poles of the magnets could be reversed so that the south poles of magnets 106 and 110 are adjacent each other and the north poles of magnets 110 and 114 are adjacent. As commonly understood, like poles between two magnets create opposing magnetic forces exerted on the magnets. By contrast opposite poles attract. Therefore, because the north pole of movable magnet 110 is adjacent the north pole of fixed magnet 106, a force results tending to push movable magnet 110 away from fixed magnet 106, and towards fixed magnet 114. Similarly, because the south pole of movable magnet 110 is adjacent the south pole of fixed magnet 114, another force results tending to push movable magnet 110 away from fixed magnet 114 and towards fixed magnet 106. If the two opposing forces on movable magnet 110, created from the magnetic interaction between fixed magnets 106, 114 and movable magnet 110, are equal in magnitude (and opposite in direction) moving magnet 110 will be forced to the center position in cavity 104 as shown in FIG. 1. Thus, the movable magnet is held stationary within cavity 104 by fixed magnets 106, 114 when the accelerometer is not subjected to acceleration forces.

It is also known that a changing magnetic field in close proximity to a coil of wire will induce an electrical current in the coil of wire. A static magnetic field, that is, a magnet magnetic field whose amplitude and direction do not change, does not induce an electrical current in a coil of wire. Thus, with movable magnet 110 stationary and centered in the cavity 104 as shown in FIG. 1, no electrical current is induced in coil of wire 116, and thus the accelerometer produces a zero voltage output signal on conductors 107 and 108.

Referring still to FIG. 1, if a force is applied to one end or the other of accelerometer 100 along longitudinal axis 119, the accelerometer 100 experiences an acceleration in the direction of the externally applied force. The inertia of moving magnet 110, however, causes it to resist the acceleration experienced by accelerometer 100, resulting in movement of movable magnet 110 within cavity 104. Thus, if a force $F_1$ is applied to the left side 103 of the accelerometer 100, accelerometer 100 is forced to the right in response to the applied force. Movable magnet 110, however, resists the motion of accelerometer 100 thus creating a relative motion for movable magnet 110 to the left, i.e. in the opposite direction of the applied force $F_1$. Similarly, accelerometer 100 will move to the left within the cavity if a force $F_2$ is applied to the right side 109 of accelerometer 100.

Movement of movable magnet 110 within coil of wire 116 causes a changing magnetic field which induces an electrical current in coil of wire 116. Further, the amount of electrical current induced in coil 116 is proportional to the magnitude of the acceleration experienced by accelerometer 100. The voltage across conductors 107 and 108 thus is proportional to the acceleration experienced by accelerometer 100. The opposing magnetic forces caused by fixed magnets 106, 114 force movable magnet to its center position after the externally applied force is removed and the acceleration ceases. The magnetic forces caused by fixed magnets 106, 114 should be large enough so that movable magnet 110 does not contact either fixed magnet while the accelerometer 100 experiences acceleration.

It is preferred that two coil sections 116a, 116b are used to wrap cavity 104, rather than one continuous coil of wire from one end of the accelerometer to the other. If one continuous coil of wire were used, the magnetic flux lines (an exemplary flux line is shown as line 117) would cut through opposite ends of the coil in opposite directions generating oppositely directed currents in either end of the coil, thereby generating a net current of zero amperes. Coil section 116a preferably is wound in an opposite direction around cavity 104 from coil wire 116b. Winding the two coils section in opposite directions allows the electrical current induced in one coil section to contribute to the electrical current induced in the other coil section, and not cancel the electrical current induced in the other coil of wire as would be the case if the two coil of wire were wound in the same direction. Alternatively, the coil sections 116a, 116b may be wound in the same direction in such a way, as known to those of ordinary skill, to allow the currents induced in both coil sections to add together rather than cancel each other.

It is important for creating a larger output signal (i.e., voltage), as is desirable, that moving magnet 110 be allowed to move as freely as possible within cavity 104. To allow moving magnet 110 to move freely, it may be necessary to remove all of the air within cavity 104. That is, a vacuum would be drawn and the cavity sealed with the air pressure in the cavity preferably less than 0.1 atmosphere. Alternatively, an axial slot may be made in can 102 along one side of the cavity to provide an air path around the moving magnet.

In operation the electromagnetic accelerometer 100 of FIG. 1 preferably produces a zero output voltage when no external force is applied to the accelerometer 100. When accelerometer 100 experiences an acceleration resulting from an external force having a component along longitudinal axis 119, the output voltage on conductors 107 and 108 becomes positive (or negative depending on the direction of the applied force resulting in the acceleration). If an oscillatory force is applied to accelerometer 100, moving the accelerometer back and forth along longitudinal axis 119, the output voltage on conductors 107 and 108 will oscillate between positive and negative voltage values. In this case, the acceleration can be determined by measuring the peak-to-peak voltage across conductors 107 and 108.

The magnitude of the output voltage is proportional to the magnitude of the magnetic field of moving magnet 110. Thus, if higher voltage output signals are desired, the strength of the magnetic field associated with magnet 110 should be increased. The magnetic field of magnet 110 generally can be increased by increasing the mass of the magnet (i.e., making the magnet 110 larger) or any other technique known to those of ordinary skill. A larger moving magnet may force the overall size of electromagnet accelerometer 100 to be increased.

Additionally, the accelerometer's output voltage can be increased by including more than one coil of wire around cavity 104. Two or more coils can be coaxially wrapped with one coil wrapped abut the other coil around the cavity with the current induced in each coil contributing to the currents induced in the other coil(s).

It should also be recognized that the electromagnetic accelerometer of the preferred embodiment is a single axis device meaning it generates maximum output signals for accelerations along longitudinal axis 119. Nevertheless, the accelerometer will still produce an output signal, albeit at a lower voltage level, for accelerations at angles (other than 90°) to axis 119. Two or three accelerometers mounted at 90° angles to each other can be used to provide two or three axis accelerometer devices.

Figure 2:
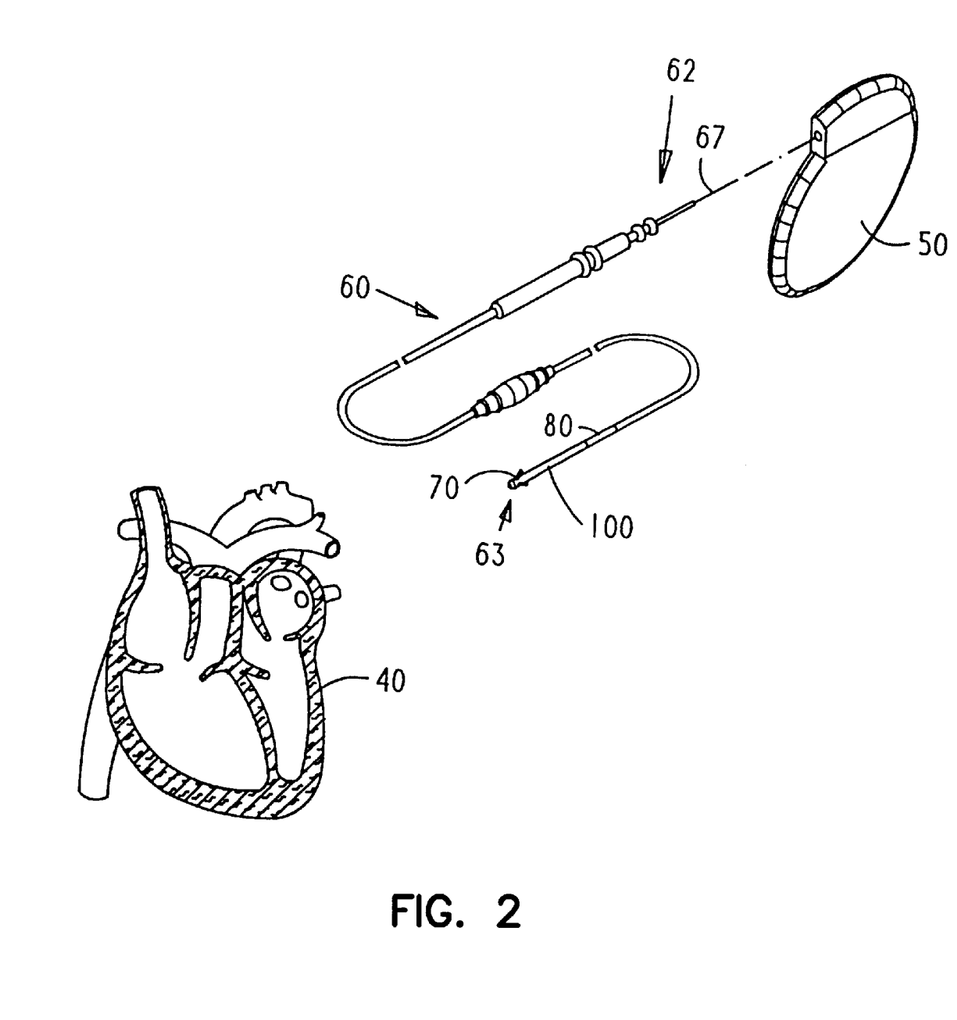
FIG. 2 is a perspective view of a pacemaker and lead which incorporates the accelerometer of FIG. 1.

The electromagnetic accelerometer of the preferred embodiment can be used advantageously in an implantable medical device, such as a pacemaker or defibrillator (both referred to hereafter as a pacemaker). Referring now to FIG. 2, a pacemaker 50 includes a lead 60 in which one end 62 of the lead couples to pacemaker 50 (referred to as the "proximal" end) and the other end 63 (the "distal" end) couples to the patient's heart 40. The distal end of the lead coupled to the patient's heart includes one or more electrodes. The lead 60 in FIG. 2 includes a tip or cathode electrode 70 and ring or anode electrode 80. Electrodes 70 and 80 couple to pacemaker 50 via conductors (not shown) within lead 60. An electromagnetic accelerometer 100 preferably is disposed within lead 60 between electrodes 70 and 80, rigidly affixed to electrode 70, or with electrode 70 being a portion of the outer surface of accelerometer 100.

The mass of the suspended magnet 110 and the spring like action of magnets 106 and 114 together with the damping from sliding, or an functional forces or magnetic braking of coil 116 forms a mechanical filter which shapes the frequency response of the acceleration signals developed. The design is chosen preferably to enhance motions in the frequency range 3–30 Hz.

In accordance with standard implantation techniques, tip electrode 70 is inserted into the myocardium of a chamber of the heart. As the wall of the heart in which tip electrode 70 is inserted moves, such as when that chamber of the heart contracts, accelerometer 100 senses the heart wall acceleration and generates an output voltage proportional to the acceleration of the chamber wall. The output voltage from accelerometer 100 is transmitted through lead 60 to pacemaker 50 which measures and processes the voltage output by accelerometer 100. Pacemaker 50 may use the accelerometer's output voltage to determine capture verification, measure various physiological parameters, and the like.

Figure 3:
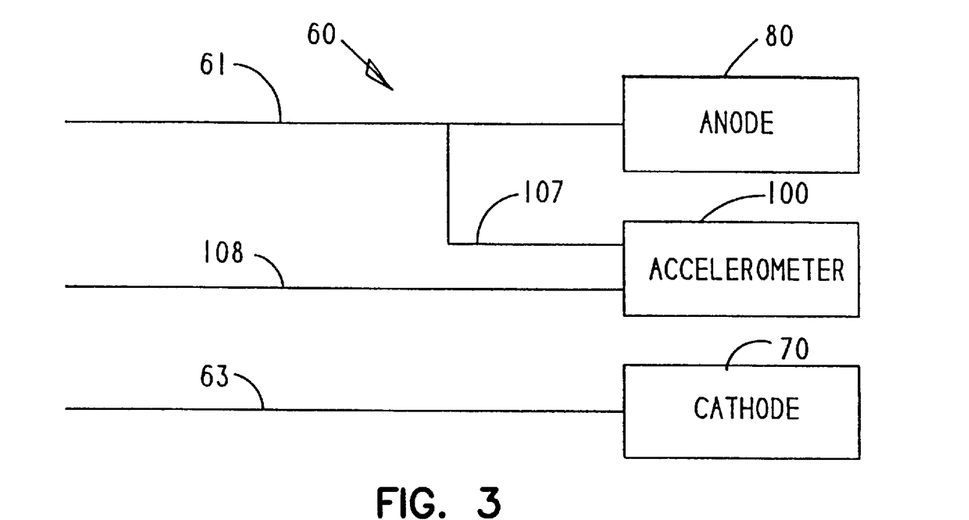
FIG. 3 is a schematic wiring diagram of a pacemaker lead including an accelerometer in accordance with a preferred embodiment.

Referring now to FIG. 3, a schematic wiring diagram of lead 60 is shown including the anode 80, electromagnetic accelerometer 100, and cathode 70. Conductor 61 couples anode 80 to the pacemaker through lead 60. Similarly, conductor 63 couples cathode 70 to the pacemaker. By connecting conductor 107 from accelerometer 100 to conductor 61, only one extra conductor 108 is required in lead 60. The accelerometer 100 constructed in accordance with a preferred embodiment thus advantageously shares one of the existing conductors in the lead, and that requires only one extra conductor in lead 60. Moreover, in requiring only one extra conductor in a cardiac lead, the increased risk of conductor breakage within a lead is kept to a minimum.

Figure 4A:
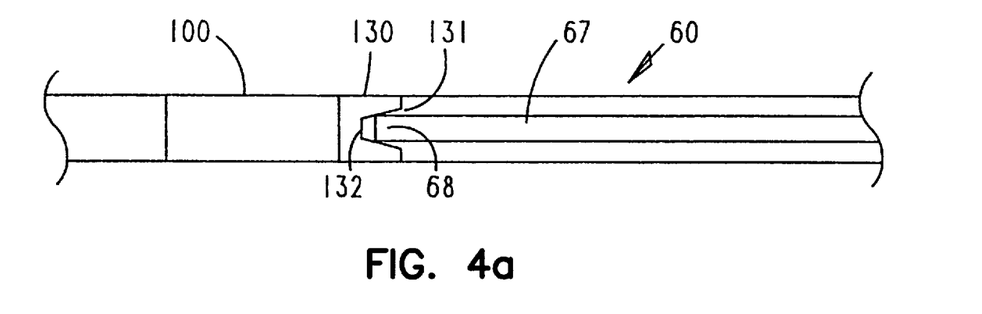
FIG. 4a is a cross-sectional view of the accelerometer of FIG. 1 incorporated into a pacemaker lead with an adapter for receiving a steering stylette.

Referring again to FIG. 2, a steering stylette 67 is axially disposed through lead body 60. Steering stylettes are commonly used when implanting leads to provide the surgeon the ability to steer the distal end of the lead through an appropriate path from the pacemaker to the chamber of the heart in which the electrode in the distal end of the lead is to be implanted. Once implanted, the steering stylette 67 is removed and the surgeon then connects lead 60 to pacemaker 50. Accordingly, it may be preferred to include an adapter within the accelerometer to provide a mating surface against which the stylette contacts. Referring now to FIG. 4a, accelerometer 100 is shown provided in a cardiac lead 60. Stylette adapter 130 preferably is included as part of accelerometer 100. Stylette adapter 130 includes a contact surface 132 having an opening 131 for receiving the distal end 68 of stylette 67. Once the lead is properly implanted in the appropriate cardiac tissue, the surgeon removes the stylette, and the accelerometer 100 and stylette adapter 130 remain in the lead 60.

It may also be preferred for the outer surface of shell 102 (FIG. 1) of the accelerometer to include a conductive portion thereby allowing the outer surface of shell 102 to serve as one of the electrodes in the lead. For example, the outer surface of shell 102 may be used as the anode electrode 80, thereby physically combining the anode and the accelerometer and reducing the complexity of the cardiac lead. In this example, shell 102 would preferably be made of titanium or IROX-coated titanium.

Figure 4B:
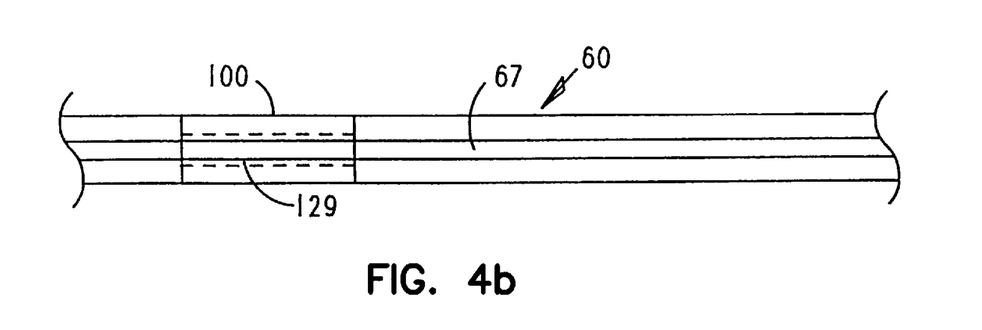
FIG. 4b is an alternative cross-sectional view of the accelerometer with a hollow longitudinal portion for receiving a steering stylette.

Referring to FIG. 4b, it may be preferred for the accelerometer 100 to include a hollow longitudinal center portion 129 for receiving the steering stylette 67. As such, the steering stylette may thus be pushed through the accelerometer 100 and couple to a tip electrode. In this embodiment, the magnets 106, 110, 114 are toroidal or do-nut shaped to allow for the stylette to pass through the center whole of the magnets. An inner rigid tube is disposed between the stylette and the inner surface of the magnet's holes to prevent the stylette from interfering with the magnets.

Providing an accelerometer in accordance with the preferred embodiment in the distal end of the lead 60 is useful for capture verification, and determining various hemodynamic parameters. Alternatively, or additionally, an accelerometer of the present invention can be included within the can of the pacemaker, thereby providing, for example, a body activity sensor. It may be desired, in fact, to include both an accelerometer in the lead and another accelerometer in the can.

Figure 5:
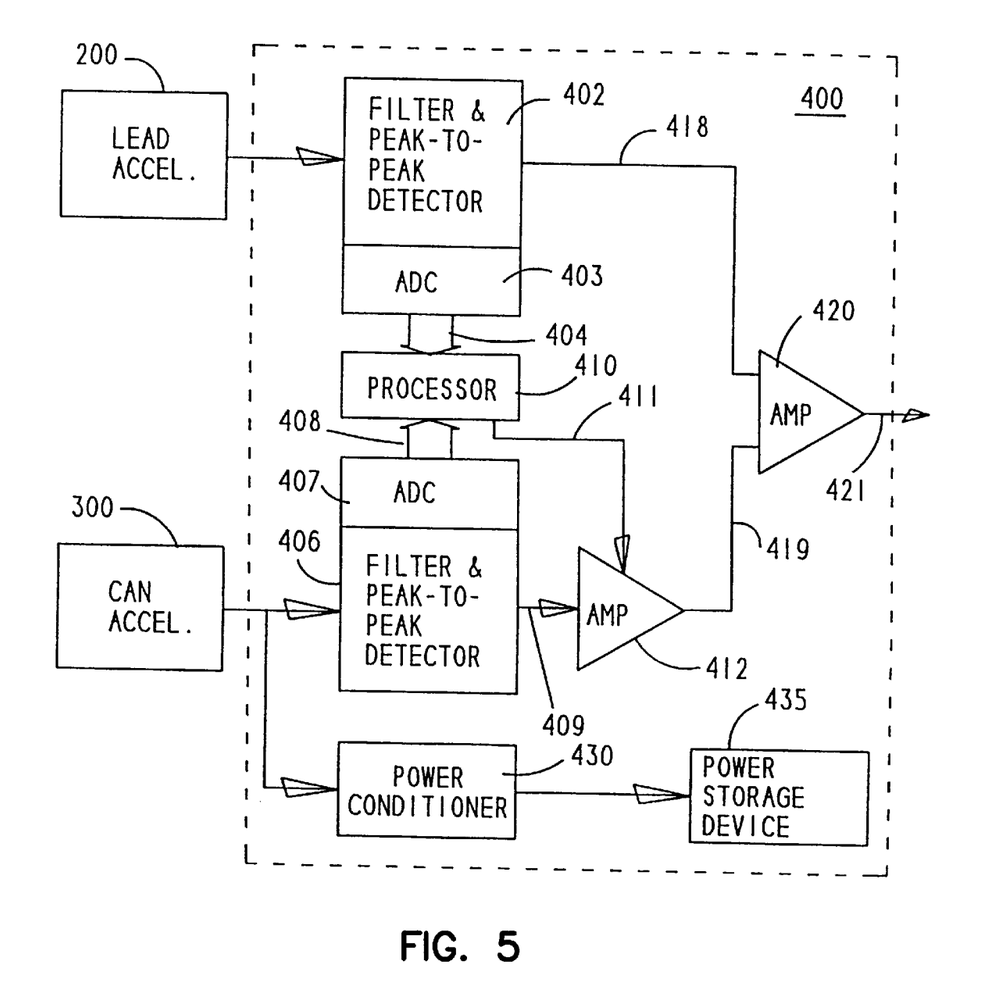
FIG. 5 is a block diagram of the electronics of a pacemaker constructed in accordance with the preferred embodiment for processing acceleration signals from two accelerometers and using the acceleration signal from one accelerometer as a body motion compensator and power source.

Referring now to FIG. 5, a block diagram 400 of a pacemaker processes signals from two accelerometers 200 and 300. Accelerometer 200 preferably is included in a cardiac lead and accelerometer 300 preferably is included within the pacemaker's can. Accelerometers 200, 300 are identical to accelerometer 100 previously described with reference to FIG. 1. The block diagram 400 generally includes a filter and peak-to-peak detector 402, 406 for each accelerometer 200, 300, a processor 410, amplifiers 412 and 420, power conditioner 430, and power storage device 435. Filter and peak-to-peak detectors 402, 406 provide low pass filtering and determine the peak-to-peak voltage range from the output signals from each accelerometer in accordance with the known techniques. Each filter and peak-to-peak detector 402, 406 includes an analog-to-digital converter 403, 407. The output of each analog-to-digital converter 403, 407 is provided to processor 410. The analog output of filter and peak-to-peak detector 402 is provided on line 418 to amplifier 420. The analog output of filter and peak-to-peak detector 406 is provided on line 409 to amplifier 412. The output signal from amplifier 412 is provided as an input signal to amplifier 420. Amplifier 420 amplifies the difference between the signals on lines 418 and 419 and provides an output signal on line 421.

The analog-to-digital converters 403, 407 digitize the analog output signals from filter and peak-to-peak detectors 402, 406 and provide the digitized data on digital lines 404, 408. Processor 410 interprets the digital values on digital lines 404 and 408 from analog to digital converters 403, 407 and, in response, controls the gain of amplifier 412 via lines 411 in accordance known techniques.

The pacemaker 400 of FIG. 5 is particularly useful for avoiding the detection of false positive signals in which a pacemaker confuses an acceleration signal from a lead-based accelerometer as a heart wall acceleration (i.e., contracting chamber) when the signal, infact, was the result of general body activity and not a contracting heart chamber. It should be apparent that both lead accelerometer 200 and can accelerometer 300 will experience motion of the patient's body. Thus, general body activity causes an acceleration that is common to both accelerometers. Accordingly, amplifier 420 amplifies only the difference between the output signals from accelerometers 200 and 300, thereby canceling the common body activity acceleration experienced by both accelerometers 200, 300. The output signal from amplifier 420 on line 421 thus represents the acceleration experienced by lead accelerometer 200 resulting only from heart wall accelerations and not general body activity.

It should be recognized that the output voltage from lead accelerometer 200 and can accelerometer 300 will have different magnitudes for a variety of reasons. First, each accelerometer only detects the acceleration along its longitudinal axis 119 shown in FIG. 1. In general, lead accelerometer 200 and can accelerometer 300 will be included in the patient's body in different orientations and thus, even if the two accelerometers were identical, the magnitude of their output signals will be different. Further, it may be desired to use the can accelerometer 300 as a power source, as will be explained in more detail below. If desired as a power source, the can accelerometer 300 may be constructed so that it's output voltage and current are larger than the output voltage from lead accelerometer 200 given an identical acceleration. Thus, before amplifier 420 can subtract the signals on lines 418 and 419 (and amplify the difference), the two input signals to amplifier 420 must be calibrated to each other. Processor 410, in accordance with the calibration method 500 discussed below with respect to FIG. 6, determines an appropriate gain correction factor for the can accelerometer 300 and varies the gain of amplifier 412 accordingly, thereby calibrating the two accelerometers to each other.

Figure 6:
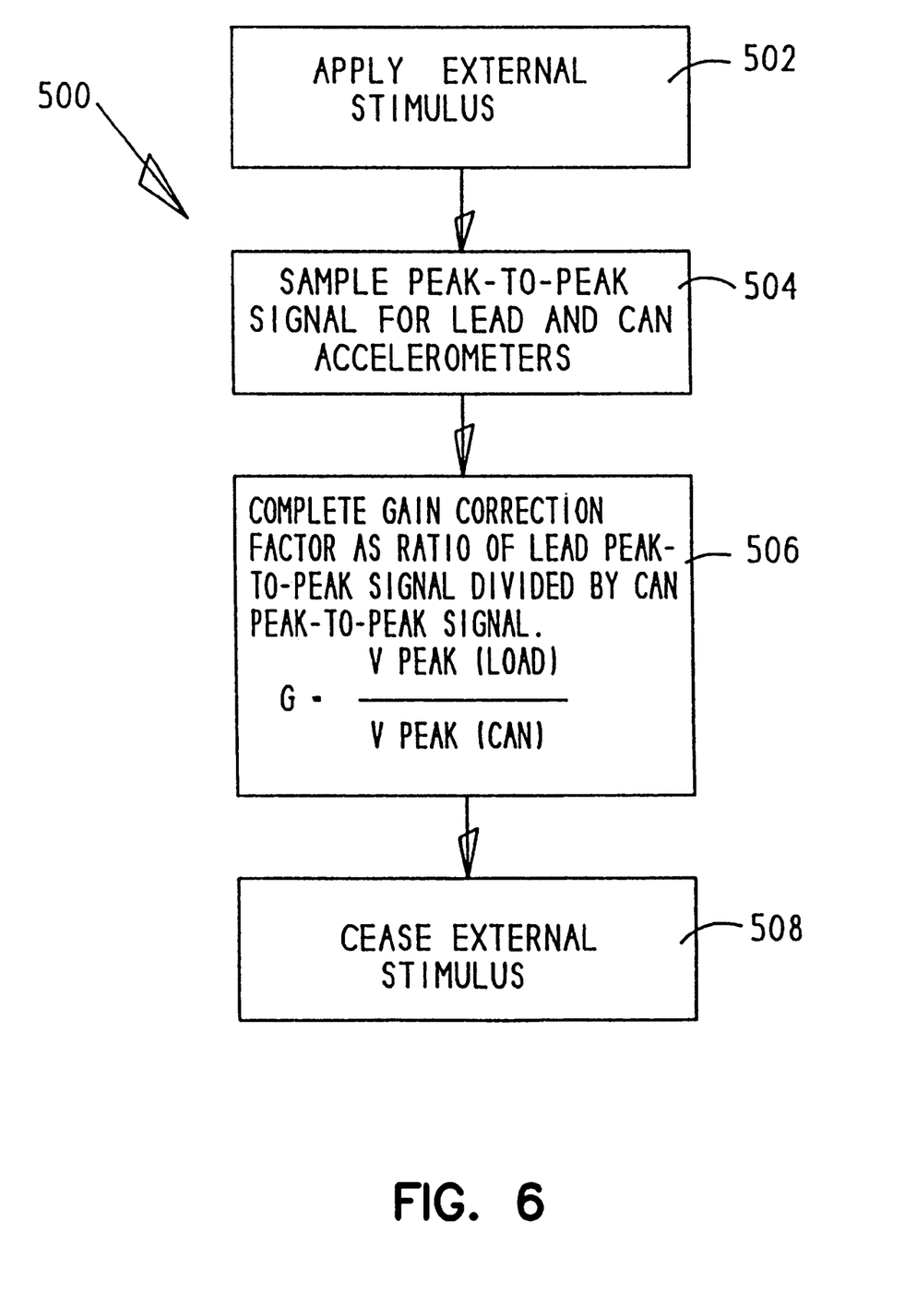
FIG. 6 is a method for calibrating the accelerometers of FIG. 5.

Referring now to FIG. 6, calibration routine 500 preferably is performed by processor 410 (FIG. 5) to determine an appropriate gain correction factor for amplifier 412. In step 502 an external acceleration stimulus is applied to the patient, thereby providing a common acceleration signal to both lead and can accelerometers 200 and 300. In step 504, the peak-to-peak voltages for the output signals from both accelerometers are determined and in step 506 a gain correction factor is calculated. The gain correction factor is calculated preferably as the ratio of the peak-to-peak lead accelerometer output voltage to the peak-to-peak can accelerometer output voltage. Finally, in step 508 the external acceleration stimulus is ceased. After completing calibration routine 500, processor 410 programs amplifier 412 to have a gain corresponding to the gain correction factor, G. The circuit of FIG. 5 and the calibration of routine to FIG. 6 can easily be modified to calibrate more than two accelerometers in a multi-lead pacemaker system, for example, that includes an accelerometer in each lead and one or more additional accelerometers in the can.

The calibration routine of 500 can be performed during implantation or in a post-surgical procedure. The external stimulus in step 502 can be performed using any one of a variety of techniques such as having the patient lie supine on a vibrating table. A command from an external pacemaker programmer (not specifically shown) preferably triggers the pacemaker 400 to enter a calibration mode of operation in which the calibration routine 500 is performed.

It should be recognized from the discussion above that the accelerometers 100, 200, 300 of the preferred embodiment generates a voltage (i.e., electrical power) in response to an acceleration. If the output voltage from the electromagnetic accelerometer is large enough, preferably at least 2–3 volts, the accelerometer's signal will be sufficient to provide useful electrical power to directly operate at least some of the pacemaker's electronics. Referring again to FIG. 5, the output voltage from the can accelerometer 300 is provided to a power conditioner circuit 430. Power conditioner 430 converts the voltage waveform from the can accelerometer 300 into a useable form for storage and power storage device 435. As such, the power conditioner 430 preferably includes a rectification and voltage multiplier and/or voltage regulator, generally in accordance with known circuit implementations. Power storage device 435 may include a battery or capacitor for storing the conditioned output voltage from power conditioner 430. The electrical energy stored in power storage device 435 may be used to operate some of the pacemakers electronics, such as refreshing dynamic random access memory.

While preferred embodiments of this invention have been shown and described, modifications thereof can be made by one skilled in the art without departing from the spirit or teaching of this invention. The embodiments described herein are exemplary only and are not limiting. Many variations and modifications of the system and apparatus are possible and are within the scope of the invention. Accordingly, the scope of protection is not limited to the embodiments described herein, but is only limited by the claims which follow, the scope of which shall include all equivalents of the subject matter of the claims.

What is claimed is:

1. An accelerometer, comprising:
   a rigid shell including an inner wall defining a cavity;
   a first magnet disposed within said cavity and fixedly mounted with respect to said shell;
   a second magnet slidingly disposed within said cavity; and
   a third magnet disposed within said cavity, fixedly mounted with respect to said shell and spaced apart from said first magnet;
   said second magnet being between said first and third magnets and reciprocating between said first and third magnets; and
   means for detecting movement of said second magnet within said cavity.

2. An accelerometer as in claim 1 wherein said first, second, and third magnets are arranged colinearly within said cavity so that said first and second magnets include a first pair of adjacent surfaces and said second and third magnets include a second pair of adjacent surfaces.

3. An accelerometer as in claim 2 wherein said magnets are arranged within said cavity so that said first pair of adjacent surfaces include like poles of said first and second magnets and said second pair of adjacent surfaces include like poles of said second and third magnets.

4. An accelerometer as in claim 3 wherein said shell includes a longitudinal axis and said second magnet moves along said longitudinal axis relative to said cavity in response to an acceleration.

5. An accelerometer as in claim 4 further including a coil of conductive wire wrapped around said cavity, wherein an electrical current is induced in said coil of wire when said second magnet moves relative to said cavity.

6. A pacemaker lead, comprising:
   a first electrode; and
   an electromagnetic accelerometer, said electromagnetic accelerometer comprising
     a rigid shell including an inner wall defining a cavity,
     a first magnet disposed within said cavity and fixedly mounted with respect to said rigid shell;
     a second magnet slidingly disposed within said cavity; and
     a third magnet disposed within said cavity and fixedly mounted with respect to said rigid shell; said second magnet reciprocating between said first and third magnets; and
     means for detecting movement of said second magnet within said cavity.

7. A pacemaker lead as in claim 6 wherein said first, second, and third magnets are arranged colinearly within said cavity so that said first and second magnets include a first pair of adjacent surfaces and said second and third magnets include a second pair of adjacent surfaces.

8. A pacemaker lead as in claim 7 wherein said magnets are arranged within said cavity so that said first pair of adjacent surfaces include like poles of said first and second magnets and said second pair of adjacent surfaces include like poles of said second and third magnets.

9. A pacemaker lead as in claim 8 wherein said shell include a longitudinal axis and second magnet moves along said longitudinal axis relative to said cavity in response to an acceleration.

10. A pacemaker lead as in claim 9 further including a coil of conductive wire wrapped around said cavity, wherein an electrical current is induced in said coil of wire when said second magnet moves relative to said cavity.

11. An implantable medical device, comprising:
    a housing;
    at least one lead coupled to said housing and including a first electrode;
    at least one electromagnetic accelerometer producing an output signal; said electromagnetic accelerometer further comprising a shell including an inner wall defining a cavity,
      a first magnet disposed within said cavity and fixedly mounted with respect to said shell;
      a second magnet slidingly disposed within said cavity; and
      a third magnet disposed within said cavity and fixedly mounted with respect to said shell;
      said second magnet reciprocating between said first and third magnets; and means for detecting movement of said second magnet within said cavity;
    means connected to said lead for producing an electrical stimulation; and means in electrical communication between said accelerometer and said stimulation producing means for modifying said stimulation as a function of said output signal of said accelerometer.

12. An implantable medical device as in claim 11 wherein said first, second, and third magnets are arranged generally colinearly within said cavity so that said first and second magnets include a first pair of adjacent surfaces and said second and third magnets include a second pair of adjacent surfaces.

13. An implantable medical device as in claim 12 wherein said magnets are arranged within said cavity so that said first pair of adjacent surfaces include like poles of said first and second magnets and said second pair of adjacent surfaces include like poles of said second and third magnets.

14. An implantable medical device as in claim 13 wherein said shell include a longitudinal axis and second magnet moves along said longitudinal axis relative to said cavity in response to an acceleration.

15. An implantable medical device as in claim 14 further including a coil of conductive wire wrapped around said cavity, wherein an electrical current is induced in said coil of wire when said second magnet moves relative to said cavity.

16. An implantable medical device as in claim 15 further comprising means for using said electrical current induced in said coil of wire as a power source for said implantable medical device.

17. An accelerometer, comprising:

a housing;

a first magnet retained in a fixed position within said housing and having a first end of a first predetermined polarity;

a second magnet retained in a fixed position within said housing and spaced apart from said first magnet and having a first end of a second predetermined polarity;

a third magnet in said housing and disposed between said first and second magnets such that the end of said third magnet that is closest to said first magnet is of first predetermined polarity and also such that the end of said third magnet that is closest to said second magnet is of said second predetermined polarity, said third magnet being mounted so as to be free to reciprocate between said first and second magnets, and a coil of wire for sensing motion of said third magnet, said coil including a first portion and a second portion, said first portion being disposed about the first end of the first magnet and a part of said third magnet and wound in a first direction and said second portion being disposed about the first end of the second magnet and a part of said third magnet and wound in a second direction.

* * * * *